United States Patent [19]

Dethman

[11] 4,089,066
[45] May 16, 1978

[54] FINGERNAIL PROTECTOR

[76] Inventor: Margaret L. Dethman, 2900 Fry St., Boise, Id. 83704

[21] Appl. No.: 794,749

[22] Filed: May 9, 1977

[51] Int. Cl.² .................................................. A41D 13/00
[52] U.S. Cl. .................................................................. 2/21
[58] Field of Search ............ 2/21; 223/101; D3/19 E; 16/108, 109

[56] References Cited

U.S. PATENT DOCUMENTS

| | | | |
|---|---|---|---|
| 1,516,385 | 11/1924 | Keck | 2/21 |
| 2,179,046 | 11/1939 | Lewis | 2/21 |
| 2,903,701 | 9/1959 | Robinson | 2/21 |
| 3,608,091 | 9/1971 | Wilson et al. | 2/21 |

Primary Examiner—Doris L. Troutman
Attorney, Agent, or Firm—Paul F. Horton

[57] ABSTRACT

A fingernail protector having a finger support flange; a semicircular lower shell, co-extensive with the flange; an upper semicircular cover resting upon the shell, the shell and cover defining a cylinder for encasing the distal finger joint; an exterior hinge connecting the shell and cover which permits convenient access to the fingernail; and a finger support strap having a plurality of flexible hooks on one side and a plurality of flexible loops on the other side.

3 Claims, 4 Drawing Figures

FINGERNAIL PROTECTOR

BACKGROUND OF THE INVENTION

1. Field of the Invention

This invention relates, in general, to fingernail protectors, and in particular, to protectors having a hinged opening.

2. Description of the Prior Art

The desirability of protecting the fingernails, especially after polishing, has long been recognized. Without protectors, the hand on which the fingernails have been polished is effectively immobilized for the drying period. To overcome this inconvenience a number of protectors have been devised. Principal difficulties and disadvantages of present protectors is the lack of a support flange resting under the distal most finger joint to prevent flexing of the joint, lack of complete enclosure thus permitting contact from sides and bottom, and the general discomfort and inconvenience of existing straps to hold the device to the finger.

SUMMARY OF THE INVENTION

The present invention comprises a fingernail protector having a finger support flange, a cylindrical encasement opening by means of a hinge, and a finger support strap having a plurality of hooks on one side and a plurality of loops on the other side, said hooks and loops engageable by pressing together thereby permitting exact finger encirclement.

It is therefore an object of the present invention to provide a fingernail protector having a finger support flange resting below the finger joint.

Another object of the present invention is to provide a fingernail protector which fully encases the distalmost joint of the finger and which is openable by means of a hinge.

A further object of the present invention is to provide a fingernail protector which includes a finger strap adjustable to fingers of varying sizes.

More particularly, it is an object of the present invention to provide a fingernail protector having a finger strap having a plurality of hooks on one sie and a plurality of loops on the other side, the hooks adapted to engage the loops to hold the strap in a fixed encircling position.

Other objects will become apparent and a more through and comprehensive understanding may be had from the following description taken in conjunction with the accompanying drawings forming a part of this specification.

DETAILED DESCRIPTION OF THE INVENTION

Figure 1:
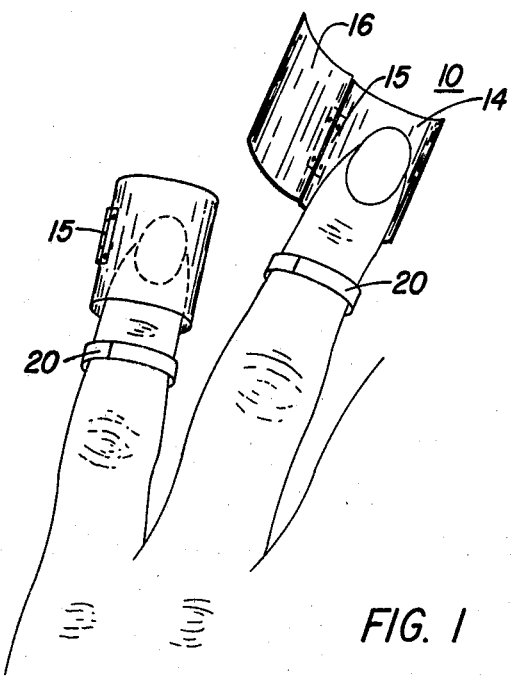
FIG. 1 is a perspective view of an embodiment of the present invention shown in the open and closed position

Referring now to the drawings, a fingernail protecting device 10 made according to the present invention is disclosed. Fingernail protector 10 includes finger support flange 12, lower semi-circular shell 14, upper semi-circular cover 16, hinge 15, and finger support strap 20.

Shell 14 is a semicircular tube which may be made of any suitable material such as plastic, metal, or wood, it only being necessary that the material not be so flexible that it is easily distorted. The diameter of the shell may be varied to accommoate fingers of different sizes, a diameter of between 2 and 2.5 cm. being a desirable size. Shell 14 contains at one terminal end a finger support flange 12 which may be attached by welding, gluing or otherwise, it being preferred that flange 12 be co-extensive with and unitary with shell 14. Flange 12 is approximately 2 cm. in length and may have a concave upper surface to maximize surface area of the flange to the underside of the finger. The flange is designed to come into contact with the distalmost finger or thumb joint.

Figure 2:
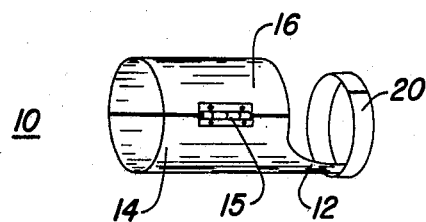
FIG. 2 is an elevated perspective view thereof.
Figure 3:
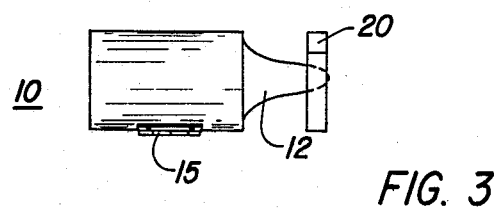
FIG. 3 is a to plan view thereof.
Figure 4:
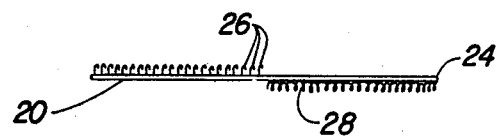
FIG. 4 is a side view of the finger strap of the present invention, shown extended and disconnected from the device

Attached adjacent the other terminal end of flange is is finger support strap 20 for encircling the finger and holding the finger in a close, tight, and yet comfortable relationship with flange 12. For this reason, strap 20, shown to advantage in FIGS. 2 and 4, is made of a thin base layer 24, preferably of nylon fabric, having a multiplicity of firm, but slightly resilient hooks 26, also made of nylon, on one side and a multiplicity of soft nylon loops 28 on the other side. Strap 20 which may be approximately 7–8 cm. in length is fastened at substantially its midpoint to flange 12. Strap 20 is caused to adjust to finger size by merely encircling the finger and pressing the hooks into the soft loops as they overlap. The hooks and loops thereby lock together and may be unlocked by simply peeling the loops and hooks apart.

Cover 16 is semicircular in form and is of equal dimensions as shell 14. Cover 16 rests on shell 14 in mirror-image orientation whereby the shell and cover define a hollow cylinder as may be readily seen in FIGS. 1 and 2. Hinge 15 connects shell 14 to cover 16 in such a manner as to maintain the cylindrical form while in the closed position. Hinge 15 is preferably mounted on the exterior side of shell 14 and cover 16 and may include frictional engagement between the moving parts of the hinge so that cover 16 may be opened and held at any desired position relative to shell 14.

Having thus described in detail a preferred embodiment of the present invention, it is to be appreciated and will be apparent to those skilled in the art that many physical changes could be made in the apparatus without altering the inventive concept and principle embodied therein. The present embodiment is therefore to be considered in all respects as illustrative and not restrictive, the scope of the invention being indicated by the appended claims rather than by the foregoing description, and all changes which come within the meaning and range of equivalency of the claims are therefore to be embraced therein.

I claim:

1. A fingernail protector comprising:
   a finger support flange;
   a semicircular shell secured adjacent a terminal end of said flange;
   a semicircular cover supported by said shell whereby said shell and said cover define a cylinder;
   hinge means connecting said shell to said cover; and
   a finger strap secured to the terminal free end of said flange, said strap adapted to encircle a finger and attach upon itself.

2. A fingernail protector as described in claim 1, wherein said finger support flange includes a concave upper surface.

3. A fingernail protector as described in claim 1, wherein said finger strap included a flexible belt having a multiplicity of hooks on one side and a multiplicity of loops on the other side, the hooks adapted to releasably engage the loops.